(12) United States Patent
Gueritault et al.

(10) Patent No.: US 7,001,572 B1
(45) Date of Patent: Feb. 21, 2006

(54) ANALYZING DEVICE WITH BIOCHIP

(75) Inventors: Thomas Gueritault, Renens (CH); Maxime Odiet, Cormondreche (CH); Jean-Claude Prelaz, Chez le Bart (CH)

(73) Assignee: Bio Merieux, L'etoile (FR)

( * ) Notice: Subject to any disclaimer, the term of this patent is extended or adjusted under 35 U.S.C. 154(b) by 575 days.

(21) Appl. No.: 10/019,946

(22) PCT Filed: Jul. 19, 2000

(86) PCT No.: PCT/FR00/02079

§ 371 (c)(1), (2), (4) Date: Feb. 25, 2002

(87) PCT Pub. No.: WO01/05504

PCT Pub. Date: Jan. 25, 2001

(30) Foreign Application Priority Data

Jul. 19, 1999 (FR) .................................. 99 09488

(51) Int. Cl.
  *G01N 15/06* (2006.01)

(52) U.S. Cl. ................... 422/68.1; 422/55; 422/58; 422/82.05; 435/287.1; 435/288.3; 435/283.1; 435/287.2; 435/288.7

(58) Field of Classification Search ............ 435/6, 435/7.1, 4, 283.1, 287.1, 288.3, 287.2, 288.7; 422/55, 58, 50, 82.05, 68.1, 82.07; 436/518

See application file for complete search history.

(56) References Cited

U.S. PATENT DOCUMENTS

| 5,218,229 A | | 6/1993 | Farnworth |
| 6,126,899 A | * | 10/2000 | Woudenberg et al. ........ 422/50 |
| 6,140,044 A | * | 10/2000 | Besemer et al. ............... 435/6 |
| 6,716,642 B1 | * | 4/2004 | Wu et al. .................... 436/518 |

FOREIGN PATENT DOCUMENTS

| EP | 0 498 703 A1 | | 8/1992 |
| EP | 0 695 941 | * | 2/1996 |
| WO | WO 90/05910 | | 5/1990 |
| WO | WO 95/33846 | | 12/1995 |
| WO | WO 98/01221 | | 1/1998 |

* cited by examiner

Primary Examiner—Long V. Le
Assistant Examiner—Melanie Yu
(74) Attorney, Agent, or Firm—Oliff & Berridge, PLC

(57) ABSTRACT

The invention concerns a device for analyzing at least an analyte, comprising a container and a biochip defining together at least a section, attached to the container by a suitable adhesive. The biochip comprises a support, for example polyhedral, comprising an active face including an active surface, whereon are distributed and bound a plurality of ligands) to be analysed, at least a face opposite to the active face, and a transverse peripheral strip linking the active and opposite faces, comprising for example several edges. The invention is characterized in that the adhesive fixing the biochip to the container links, on one side the transverse strip of the biochip, practically excluding any other part, face or surface of the biochip, to the container, and the adhesive completely exposes the peripheral zone of the active face of the biochip.

28 Claims, 4 Drawing Sheets

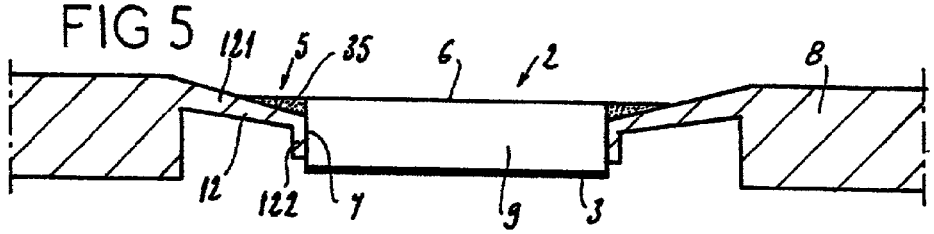
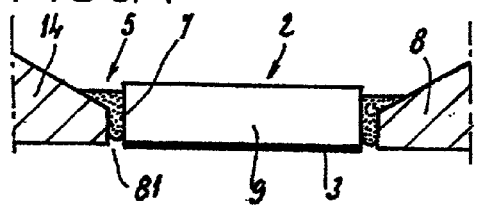
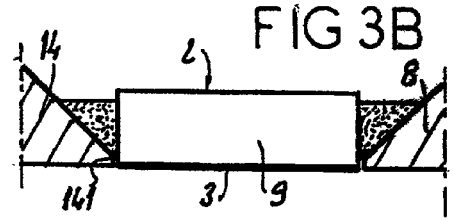
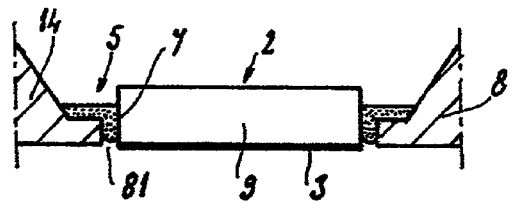
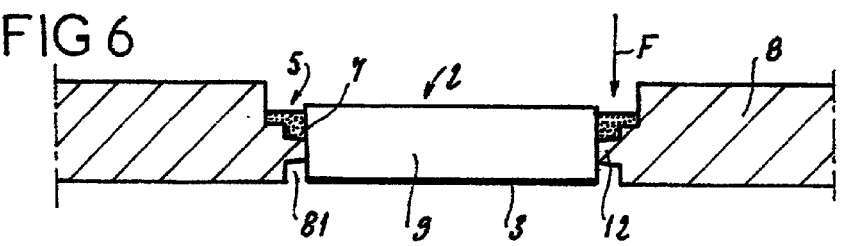
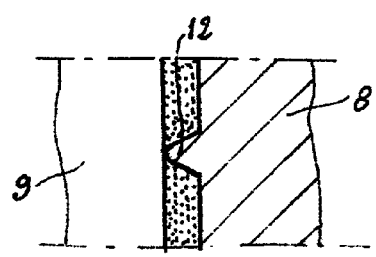

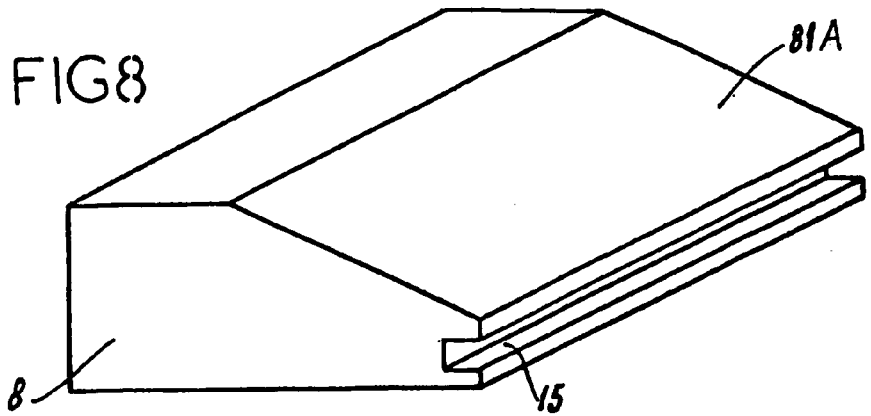
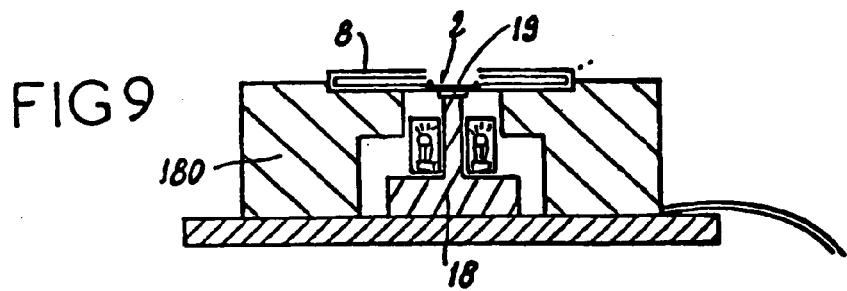
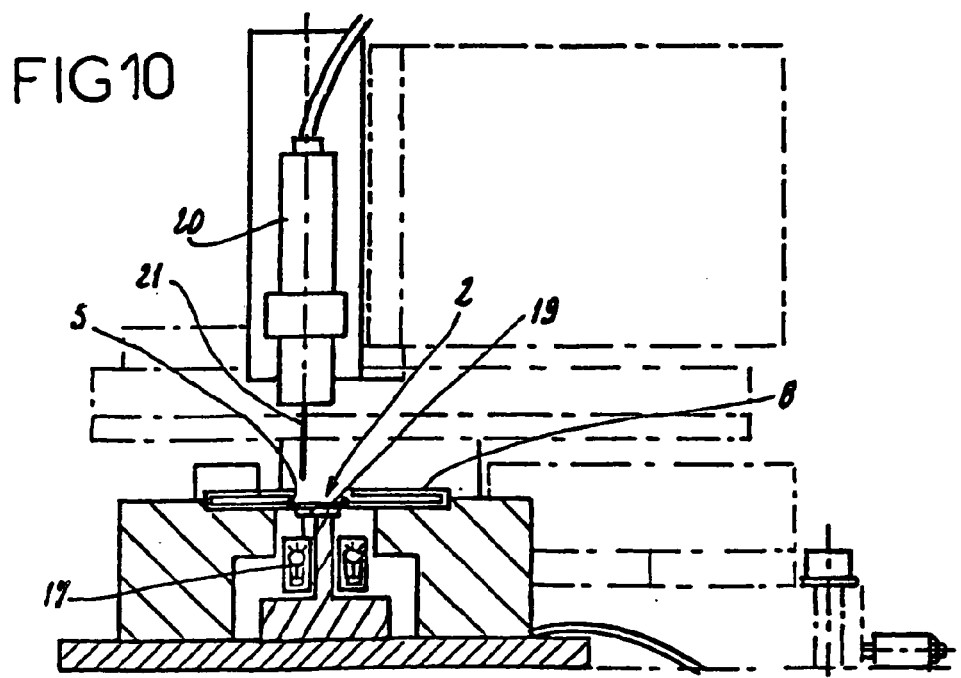

ANALYZING DEVICE WITH BIOCHIP

BACKGROUND

The present invention relates to a device for analyzing at least one analyte, comprising a container and a biochip, the latter being attached to the container by a suitable means of attachment.

The term "biochip" is intended to mean, and with reference to FIG. 1, any component comprising, in a way known per se, a support 9, in particular polyhedral in shape, for example parallelepipedal in shape. This support 9 comprises, firstly, an active face 3 comprising an active surface 31, onto which are distributed and attached a plurality of ligands 4 used for the analysis and, optionally, depending on the detection method used, a peripheral zone 32 free of ligands, secondly, at least one face 6 opposite the active face, for example parallel to the active face, and a transverse and peripheral strip 7, or edge, connecting the active 3 and opposite 6 faces, comprising, for example, several sides 71 to 74 in the case of a parallelepipedal shape.

Advantageously, the surface area of the active surface is less than 100 mm for example less than 65 $mm_2$, and preferentially less than 30 $mm_2$. The thickness of support, for example the width of the transverse strip 7, is less than 5 mm, advantageously less than 1 mm. In certain cases, the biochip support is in the shape of a cylindrical disk, in which case, the transverse strip has no edge.

Preferentially, the active surface represents at least 75% of the surface area of the active face.

The ligands may be attached in various ways, in particular by adsorption or covalence, such as for example in situ synthesis by photolithography techniques, or by a piezoelectric system, by capillary deposit of preformed ligands. By way of illustration, examples of these biochips are given in the publications by G. Ramsay, Nature Biotechnology, 16, p. 40–44, 1998; F. Ginot, Human Mutation, 10, p. 1–10, 1997; J. Cheng et al, Molecular diagnosis 1(3), p. 183–200, 1996; T. Livache et al, Nucleic Acids Research, 22(15), p. 2915–2921, 1994; J. Cheng et al, Nature Biotechnology, 16, p. 541–546, 1998, or in patents U.S. Pat. No. 4,981,783 (Augenlicht), U.S. Pat. No. 5,700,637 (Southern), U.S. Pat. No. 5,445,934 (Fodor), U.S. Pat. No. 5,744,305 (Fodor), U.S. Pat. No. 5,807,522 (Brown).

The state of the art consists of the document WO 95/33846, which describes a consumable for biological analysis, in which a biochip is attached to a plastic support. This parallelepipedal-shaped biochip comprises, on its active face, a large number, generally several thousands to several hundreds of thousands, of oligonucleotides placed at predetermined locations. Several means for attaching the biochip are described, both by adhesive bonding and by sealing. However, in all cases, part of the active face of the biochip, where the oligonucleotides are located, is used for the attachment to the plastic. In this case, the area on the active face used for attaching the biochip to the consumable is not available for oligonucleotides to be grafted onto it.

There are two constraints for the industrial application of these biochips. Firstly, the desire to reduce production costs for these biochips involves a decrease in the size of the latter, with, as an indirect consequence, a decrease in the size of the consumable, which decreases the costs of the device accordingly. Secondly, the desire to carry out several simultaneous analyses (such as detecting a panel of pathogenic agents in a biological sample, or detecting the effect of a molecule on the expression of a multitude of messenger RNAs in order to identify the metabolic pathway on which this molecule acts) with the same biochip leads to an increase in the number of ligands on the surface of the biochip. Thus, industrial logic deems that a maximum number of ligands be placed on a minimum surface area.

The technique described in application WO 95/33846 therefore has the major drawback of using part of the active face of the biochip for attaching it to a consumable, which is not compatible with the industrial constraints described above.

In addition, it is important that the optical detection should not be affected by the means of attachment.

SUMMARY

The present invention solves the problem thus posed, by providing, in general, a single means for attaching the biochip which connects, on one side, the transverse strip, or edge, of the support of said biochip, virtually excluding any other part, face or surface of said biochip, and, on the other side, the container, this being on both sides of the active face of the biochip; and this attachment means completely exposes moreover the peripheral zone of the active face of the biochip, i.e. it neither obstructs nor masks, at least in part, said active face.

The term "virtually" is intended to mean that the attachment means exposes at least 95% of the entire active face, advantageously at least 97%, and preferentially at least 99%.

According to the present invention, two scenarios should be envisaged, depending on whether, as a function of the method for detecting the ligands, the active surface merges with the complete surface of the active face, or whether a peripheral zone, free of ligands, surrounds the active surface and extends in width between said active surface and the edge of the active face.

In the first case, the attachment means exposes virtually entirely, if not completely, the active surface.

In the second case, the attachment means also exposes, virtually entirely, if not completely, the peripheral zone of the active face.

A certain number of terms used in the present invention are explained below.

The term "analytical device" is intended to mean any apparatus which allows the analysis of one or more different liquid or gaseous samples, in which the intention is to identify and/or quantify one or more analytes according to any simple or complex analytical process involving one or more different reagents, depending on the chemical, physical or biological nature of the analyte(s) sought. The technical principles defined hereinafter are not limited to a particular analyte, the only condition required being that the analyte is distributed in the sample to be analyzed, in suspension or in solution. In particular, the analytical process used may be carried out in a homogeneous, heterogeneous or mixed form. One example of application of the analytical techniques relates to immunoassays, whatever their format, by direct analysis or by competition. Another example of application relates to the detection and/or quantification of nucleic acids, comprising all the operations necessary for this detection and/or this quantification using any sample containing the target nucleic acids. Among these various operations, mention may be made of lysis, fluidization, concentration, steps for enzymatically amplifying the nucleic acids, and detection steps which incorporate a hybridization step. Patent application WO 97/02357, the content of the description of which is incorporated into the present application, explains various steps required in the case of nucleic acid analysis.

The term "ligand" is intended to mean any biological or chemical species capable of reacting specifically with a receptor present on the analyte. By way of example of a ligand, mention may be made of an antigen, an antigen fragment, a peptide, an antibody, an antibody fragment, a hapten, a nucleic acid, a nucleic acid fragment, a polynucleotide, a hormone, a vitamin, a sugar, a polysaccharide, a chelator, a drug, a cofactor and a chemical molecule capable of binding by covalence or by adsorption. Advantageously, the ligands attached to the biochip are nucleic acids, and preferentially oligonucleotides, and are attached to the biochip by covalent coupling. In a preferential embodiment, at least 400 different oligonucleotide sequences, and preferentially at least 1 000, are attached per $cm^2$ of the solid support of the biochip.

The solid support should be suitable for the attachment of the ligands. Natural or synthetic materials, which may or may not be chemically modified, may be used as a solid support, in particular polymers such as polyvinyl chlorides, polyethylenes, polystyrenes, polyacrylates or polyamides, or copolymers based on monomers of the styrene type, unsaturated carboxylic acid esters, vinylidene chloride, dienes or compounds having nitrile functions (such as acrylonitrile); inorganic materials such as silica, quartz, glass, ceramics; metal derivatives. In particular, the solid support is made of nonporous material. In a particular embodiment, the solid support is made of a material which is transparent to light, and in particular glass or derivatives.

The "container" is defined as the piece or set of pieces allowing the analysis to be carried out, and to which the biochip is attached, the container and said biochip delimiting together at least one reaction compartment. In particular, this container allows the introduction of a fluid, and in particular of the liquid in which the analyte(s) to be analyzed is (are) located, and makes it possible to delimit at least one reaction compartment so as to promote the reaction between the ligands and the analyte(s).

According to a variant of the invention, the attachment means ensures that the reaction compartment is leaktight with respect to the outside.

Preferentially, the active surface faces the inside of the container so as to allow contact between the liquid medium, the analysis of whose content is desired, and the ligands attached to this active surface, and the opposite face faces the outside of the container.

By way of example, this container is a single-use consumable as described in patent applications WO 95/33846, WO 97/02357 and WO 97/27324. However, it may also be reused. The content of the description of these abovementioned patent applications is considered to be incorporated into the description of the present invention. In a preferential embodiment according to the invention, the container is made of a plastic material, such as polypropylene or polystyrene, and it is obtained by molding. According to a variant of the invention, surface treatment may be carried out on the container, especially if the container is made of polyolefin, and in particular if the container is made of polypropylene, in order to increase the adhesion of the adhesive on the container. This surface treatment may be a Corona treatment, flame brushing, cleaning of the surfaces, such as degreasing, or chemical etching of the surface.

In order to attach the biochip to a container, it is necessary to provide the container with a component capable of receiving the biochip. This reception zone is defined as being the window of the container. In particular, this window has a transverse profile substantially identical to that of the support of the biochip, but is slightly larger in size. The term "slightly larger" is intended to mean an interstice between the transverse strip of the biochip and the border of the window of the container, of between 2 mm and 0.05 mm, advantageously of between 0.5 mm and 0.05 mm, and preferentially of between 0.2 mm and 0.1 mm.

This interstice in particular has an even value along the transverse border of the support of the biochip, which is relatively low, either to allow the adhesive to be kept in the liquid state, by capillarity, for as long as it has not been cured, or to avoid the adhesive running if it is sufficiently viscous.

The term "attachment" is intended to mean any solution or means allowing any permanent bonding between the biochip and the container, respecting the abovementioned definition. By way of example, mention may be made of laser soldering, ultrasound soldering, microplasma soldering, induction soldering, high-frequency soldering, anodic bonding, adhesive bonding, molecular adhesion, hot-crimping, mechanical blocking by clipping, fastening by a stop system, by flexible, i.e. deformable, attachment, such as with a rubber seal.

Advantageously, the attachment is carried out by adhesive bonding, for example with multicomponent adhesives, for example, such as a dental adhesive, an adhesive based on a polymer dissolved in a solvent (polystyrene dissolved in xylene for example), polyurethane adhesives, epoxy adhesives, instant adhesives such as cyanoacrylate adhesives, UV adhesives, i.e. adhesives which cure under the action of ultraviolet radiation. Adhesives of this type are sold by the company DYMAX (Torrington Conn., USA) under the reference 128-M or the reference 1-20-270 or 1-20-280, or by the company EPOTECNY (Velizy, France) under the reference NOA 63, NOA 68, NOA 72 or NEA 121, or by the company LOCTITE (Dublin, Ireland) under the reference 3011, 3301, 3311, 3104 or 3105. Preferentially, the attachment is carried out with an adhesive which can be cured by ultraviolet radiation, such as the adhesive Dymax 1-20-280.

In a particular embodiment of the invention, the attachment means extends along the entire transverse strip of the biochip. According to a variant of the invention, and in particular when the biochip support is a rectangle-based or square-based parallelepiped, and when the attachment is performed by adhesive bonding, the adhesive seal covers the four sides and the four right angles. In a preferential embodiment of the invention in which the attachment is performed by adhesive bonding, the container has a particular structure at the level of the zone of attachment between the transverse strip of the biochip and the window of the container, such as for example a beveled shape so as to allow a possible excess of adhesive to position itself on the container part. A ledge may also be present on the container in order to eliminate this possible excess of adhesive, as will be explained on the figures. This means makes it possible to store a surplus of adhesive without it overflowing onto the peripheral zone of the biochip.

Still in this embodiment by adhesive bonding, and with the aim of improving the mechanical resistance of the adhesive seal, a concavity may be made on all or part of the surround of the window of the container, such as for example a groove or a channel. The adhesive, by curing inside at least part of the concavity, improves the attachment between the container and the biochip.

In another particular embodiment of the invention, the attachment means connects two opposite zones of the transverse strip of the biochip. In this case, along the transverse strip, the attachment means is discontinuous between the biochip and the container.

According to another variant, the attachment means connects four zones of the transverse strip of the biochip, the four zones being distributed substantially symmetrically so as to increase the rigidity, and therefore the mechanical strength, of the analytical device.

According to another variant of the invention, the attachment means comprises means which are flexible at the level of the window of the container, and exert a pressure on the transverse strip of the biochip so as to facilitate the positioning of said biochip. For example, a window with a particular geometry is produced on the container when it is injected with a plastic material. These flexible means are designed to receive the biochip and to maintain it in place. These means should be sufficiently flexible to allow the insertion of the biochip, with moderate force, but sufficiently rigid to allow good reproducibility of insertion without, however, being brittle.

The function of these means is to attach the biochip or to maintain it in place, before carrying out the definitive attachment. By way of example, these means maintain the biochip in place by virtue of the pressure exerted on the four sides of the square-based parallelepipedal shape, long enough to place a line of adhesive of the UV type. Once the curing has taken place, the attachment of the biochip to the container is complete.

According to a variant of the invention, the flexible means consist of two interdependent components, namely a first component, or intermediate component, inclined relative to the opposite face of the biochip, and a second component, or end component, perpendicular to said opposite face, and which presses the transverse strip of the biochip.

According to another variant of the invention, the flexible means comprise claws, the cross section of which is substantially triangular. These claws exert a pressure on the transverse strip, or edge, of the biochip.

According to a variant of the invention, the biochip support consists of a material which is transparent to light, such as for example glass or glass derivatives. This variant is particularly advantageous for optically reading the analytical reaction, such as for example reading fluorescence through the glass.

With the attachment solution of the present invention, the active surface of the biochip, where the ligands are attached, may start as close as possible to the border of the support. The wall of the container may block some of the light emitted during the revelation. This limitation has two consequences: it locally decreases the spatial resolution of the biochip and locally decreases the collective intensity, so locally decreases the sensitivity of the detection dynamics. There is therefore a margin m which must be respected, belonging to the peripheral zone 32, which is the distance between the edge of the biochip and the active surface where the ligands are grafted. The calculation of this margin is related to the numerical aperture of the optic, and to the thickness and index of the glass of the biochip. If the numerical aperture of the optic is denoted NA, the refractive index of the glass is denoted n and the thickness of the glass is denoted e, the optical margin m is equal to e.tg [arcsin (NA/n)]. By way of example, for a glass thickness of 0.7 mm and an index of 1.46, the margin m varies between 255 and 548 $\mu$m, for optics with a numerical aperture of between 0.5 and 9.

In the most unfavorable case, for a biochip with a square active face having a surface area of 25 mm$^2$, the surface area of the peripheral zone 31 may be decreased to 9.9% of the surface area of the active face 3; whereas, prior to the invention, with a conventional attachment means, this same surface area may represent up to 80% of the surface area of the active face 3.

The ligands 4 may be distributed over at least 75% of the surface area of the active face of the biochip, and advantageously at predetermined positions. It is clear that this margin, in the case of the present invention, is minimal, since the attachment means according to the present invention virtually completely exposes the peripheral zone, both on the active face and on the opposite face.

The invention also relates to a process for attaching a biochip to a container, so as to produce an analytical device, characterized in that the biochip is maintained opposite the container, in that a liquid adhesive seal is distributed between the transverse strip of the biochip and the container, and in that the adhesive is cured by ultraviolet radiation.

In a particular embodiment of the invention, the biochip is arranged relative to the container so as to place the transverse strip of the biochip opposite the frame of the window of the container and allow the attachment.

Advantageously, two positioning means are available, one for the biochip and one for the container.

These positioning means may consist of a block, for example metal block on which the container rests. In a particular embodiment of the invention, a means for maintaining the container and/or the biochip in place consists in applying a vacuum using at least one orifice placed on the block. A means for positioning the biochip may consist of a support, for example a cylindrical support, on which the biochip rests, and which has at least one orifice opening out onto the surface in contact with the biochip, in order to apply a vacuum to maintain the latter. The movements of these positioning means may be controlled by a robot along the x, y and z axes. A positioning precision of the order of ±0.2 mm may be easily attained, insofar as the positioning references can be located in automatic mode, either by artificial vision or mechanically. In the case of optical reading, such as for example reading by fluorescence with a CCD camera or a laser, the flatness of the active surface is important, such as for example with a tolerance of 50 micrometers along the diagonal so as not to distort the focusing of the optical system. The present invention solves this problem, in particular in the case of the attachment by an adhesive seal, since said seal makes it possible to compensate or absorb the imperfections on the surface, both on the transverse strip, or edge, of the biochip and on the frame of the window of the container. In an embodiment in which the support of the biochip is made of glass or glass derivative, and in which said biochip is obtained from a sheet which is cut up as described in patent WO 95/33846, or by other techniques, such as the diamond saw, waterjet or laser cutting, the method of attachment by placing an adhesive seal between the biochip and the window of the container is particularly suitable. Similarly, this technique makes it possible to decrease the constraints of surface finish on the mold, when the container is obtained by molding an engineering plastic material.

The ultraviolet radiation is applied to the adhesive seal by illuminating at least one of the faces of the analytical device. In a first embodiment, when the container is made of a single component, such as for example a consumable of the cart type as described in the Applicant's patent application FR 2749663, the container is provided with a window for putting the biochip in place. After the biochip has been put in place opposite the window of the container, and the adhesive seal has been deposited, the curing is carried out in a step of to 40 seconds.

In a second embodiment, in which the container is made of two components, the adhesive seal is cured in two steps. After the container and the biochip have been put in place using the positioning means, a first step consists in pre-curing the spot of adhesive by W irradiation for a short time, between 2 and 30 seconds, and advantageously between 5 and seconds. In a second step, the adhesive is cured by UV irradiation from the other side, over a period of time of between 5 and 40 seconds, and advantageously between 15 and 30 seconds. These times vary depending on the nature of the adhesive and on the power of the irradiation lamp, and are determined by those skilled in the art. A short curing time should be sought in order to increase the manufacturing process rate.

A mask is positioned between the biochip and the ultra-violet radiation in order to protect the ligands on the active face against the effect of the ultraviolet radiation, which may degrade biological or chemical molecules. In a variant of the invention, the means for positioning the biochip acts as the mask. In another variant of the invention, a finger which is adjustable in height makes it possible to protect the active face of the biochip.

BRIEF DESCRIPTION OF THE DRAWINGS

The figures and examples below are given by way of explanatory example and are in no way limiting in nature. They will make it possible to understand the invention more clearly. In the interests of clarity of the drawing, the various elements of the drawings are not represented to scale.

FIG. 2 diagrammatically represents a partial sectional view of an analytical device according to an embodiment of the present invention;

FIG. 3A diagrammatically represents a sectional view of the zone of attachment of a biochip to a container, according to a particular embodiment of the present invention;

FIG. 3B represents a preferential attachment means according to the invention, in which a means 14 for eliminating a surplus of adhesive is represented. This means, as in FIG. 3A, has a beveled shape at the level of the window 81 of the container and forms a 45° angle. Other angles may be used. Unlike FIG. 3A, the ledge 141 at the end of the bevel is in height, for example between 0.05 and 0.1 mm for a biochip thickness of 0.7 mm. The interstice between the peripheral part of the biochip and the ledge 141 is decreased such that the adhesive cannot slide into the interstice as represented on FIG. 3B. The beveled shape also makes it possible to facilitate the positioning of the needle between the container and the biochip and, in addition, makes it possible to avoid the adhesive overflowing onto the upper surface of the biochip 2. The ledge 141, combined with the interstice and the viscosity of the adhesive, makes it possible to avoid the adhesive flowing into the interstice and there-fore the adhesive overflowing onto the active face 3 of the biochip. This attachment means therefore allows optical reading over the entire active face with as large an active surface as possible;

FIG. 4 diagrammatically represents a sectional view of the zone of attachment of a biochip to a container, according to another particular embodiment of the present invention;

FIG. 5 represents a sectional view of the zone of attachment of a biochip to a container, with flexible means made of two components;

FIG. 6 represents a sectional view of the zone of attachment of a biochip to a container, with flexible means in the form of a claw;

FIG. 7 represents a view according to F from above of the claw represented in FIG. 6;

FIG. 8 represents a part of the window frame of the container, with a means for storing the surplus of adhesive in the form of a groove;

FIGS. 9 to 11 represent, respectively, a first step, a second step and a third step of the process for attaching the biochip to a container, according to a particular embodiment of the present invention;

DETAILED DESCRIPTION OF EMBODIMENTS

Figure 1:
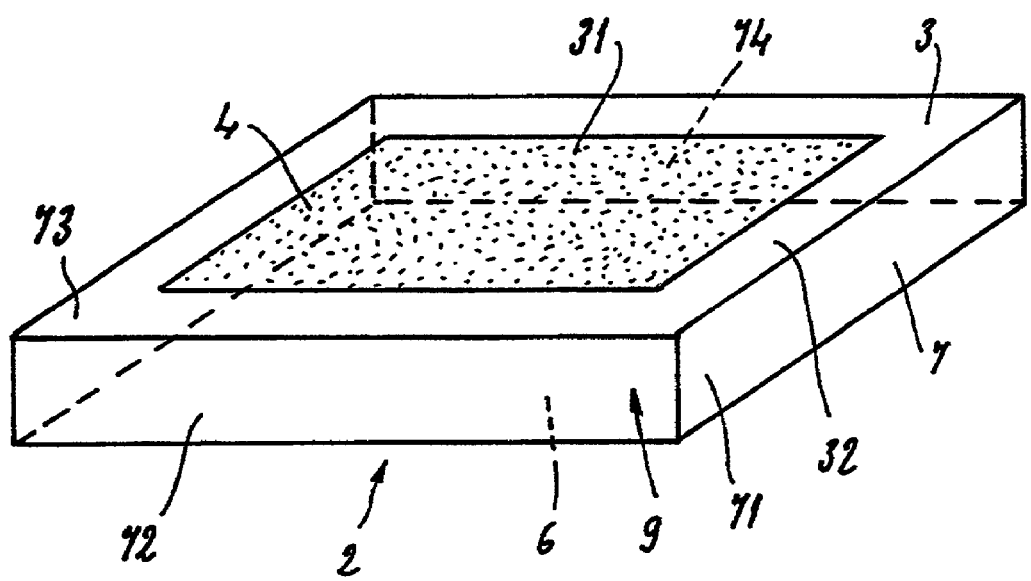
FIG. 1 represents, diagrammatically and in perspective, a biochip as considered by the present invention.

FIG. 2 shows a partial sectional view of an analytical device 1 in which a biochip 2 is attached to a container 8, via an attachment means 5. This attachment means, represented on FIG. 2 by an adhesive seal, encroaches onto neither the active face 3, on which the ligands are present, nor the opposite face 6. To do this, the adhesive seal is present between the transverse strip 7, or edge, of the biochip or, more precisely, of its support, and the frame of the window 81 of the container 8. In this embodiment, the active surface 31 of the biochip is facing the inside of the container, and the opposite face is facing the outside. A liquid, containing analytes, and not represented on the figure, may thus interact with the ligands 4 in the reaction compartment 10. The adhesive seal ensures that the compartment 10 is leaktight with respect to the outside, on this part of the container. The analytical device is represented diagrammatically, but it is clearly understood that those skilled in the art may vary the various elements of said device depending on the analysis or analyses to i be carried out, without, however, straying from the context of the invention. Among these nonrepresented elements, mention may be made of: the system for the introduction and/or for the exit of the sample, and also of possible reagents required for the analysis; a set of channels to direct the liquid; systems of valves which make it possible to control the movement of the liquid sample introduced; means for displacing liquid; means for controlling the temperature; reagent storage zones. Many descriptions of valves exist in the prior 5 art, and in particular the valves described in the patent application filed by the Applicant, dated Sep. 8, 1998, under the filing number FR-98/11383. The systems for displacing fluid, such as pumping systems, may be incorporated on the inside or on the outside of the device, such as for example diaphragm pumps (U.S. Pat. No. 5,277,556), piezoelectric peristaltic pumps (U.S. Pat. No. 5,126,022), systems for transport with ferrofluids, or electrohydrodynamic pumps (Richter et al., Sensors and Actuators, 29, p. 159–165, 1991).

Of course, a channel or several channels make(s) it possible to lead the liquid into the reaction compartment 10. These combined channels may be integrated into said analytical device 1, and allow the liquid to be sent toward other zones of the container or toward other containers, where other treatments and/or reactions may be performed. Similarly, one or more biochips 2 may be attached to the same container 8 in the case of multiple analysis.

FIGS. 3A, 3B and 4 present a sectional view of the attachment of the biochip 3 in the window 81 of the container 2, according to a particular and preferential method of attachment according to the invention, in which a means 14 for eliminating a possible surplus of adhesive is represented. In FIGS. 3A and 3B, this means 14 has a beveled shape at the level of the window 81 of the container. The angle represented is 450, but other angles may be used, as long as the adhesive can travel back along this slope. FIG. 4 represents a variant of the attachment method represented in FIG. 2, in which a ledge is added between the biochip and the beveled shape.

On these diagrams, the frame of the window 81 has an edge parallel to the transverse strip 7 of the biochip 6. This configuration has two advantages: improvement of the mechanical resistance of the window and increase in the surface area of contact for the adhesive on the container 8, which improves the attachment.

FIGS. 5 and 6 represent another embodiment of the present invention, with sectional views of the zone of attachment of the biochip 2 to the container 8, with the addition of flexible means 12 which promote the maintaining in position of the biochip. On FIG. 5, these flexible means 12 are made of two components. A first component 121 is inclined relative to the opposite face 6 of the biochip, and an end component 122 is substantially perpendicular to said opposite face and, therefore, in the case of the diagram, parallel to the transverse strip 7 of the biochip. This end component pushes against a side of the biochip so as to facilitate maintaining the biochip in place or positioning it. On FIG. 5, an attachment means represented by an adhesive seal 35 ensures the leaktightness of the attachment, but it is possible to maintain the biochip in place solely by the pressure of the flexible means 12. In order to maintain the biochip 2 in place, it is clearly understood that the pressure forces applied onto the biochip by these means 12 cancel one another out, and those skilled in the art will define the number and positioning of these means on the window 81 of the container in order to respect this constraint. In the case of a biochip with a square parallelepipedal shape, one or two means 12 opposite one another on the two sides, respectively, are suitable.

The angle between the first inclined component 121 of the flexible means 12 and the opposite face 6 of the biochip has two functions: to allow the biochip 2 to be inserted vertically so as to place it facing the container 8 without breaking said flexible means, and to allow the elimination of the surplus of adhesive, as for the beveled component described above with reference to FIGS. 3 and 4. The flexible means are produced, for example, by injection with plastic polymers such as polypropylene.

On FIG. 6, the flexible means 12 is a beveled claw, the cross section of which is substantially triangular, the tip of the claw pressing a side of the biochip. The beveled component has the same advantages as those described above for the flexible means 12. FIG. 7 shows a view of the container/ biochip junction, demonstrating the triangular cross section of this claw.

Other forms of flexible means 12 exist.

FIG. 8 shows a partial view, in perspective, of the window of the container 13, in which a concavity 15, in the form of a groove, is present in the frame 81A of the window, so as to make it possible to improve the attachment of the adhesive to the container 8. The biochip, not represented on the drawing, is a square biochip, and the drawing represents one side of the window. On the drawing, this groove is present on the entire portion of window represented, but it is possible to have this groove on only part of the surround of said window. The beveled form of the window is represented in this embodiment, but is not necessary since the groove 15 can eliminate the excess of adhesive.

FIG. 9 is a diagrammatic representation of the first step of the attachment process according to an embodiment in which the container 8 and the glass biochip 2 are put in place using the positioning means 180 and 18, respectively. A mask 19 is located between the positioning means 18 and the biochip 3.

On FIG. 10, an adhesive distributor 20 equipped with its needle 21 delivers the amount of adhesive over the entire surround located between the window 81 of the container 8 and the transverse strip 7 of the biochip 2, and pre-curing is carried out by W irradiation via the ring light 17 located below the biochip.

Figure 11:
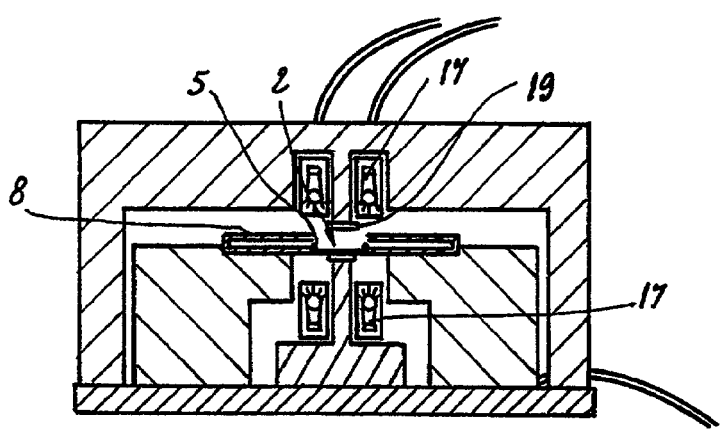

FIG. 11 represents the last step of the attachment process, during which the curing is finished by UV irradiation from above, using another ring light 17, itself also equipped with a mask 19 to protect the active face of the biochip.

EXAMPLE 1

Attachment of a Biochip to a Container by Adhesive Bonding

Figure 12:
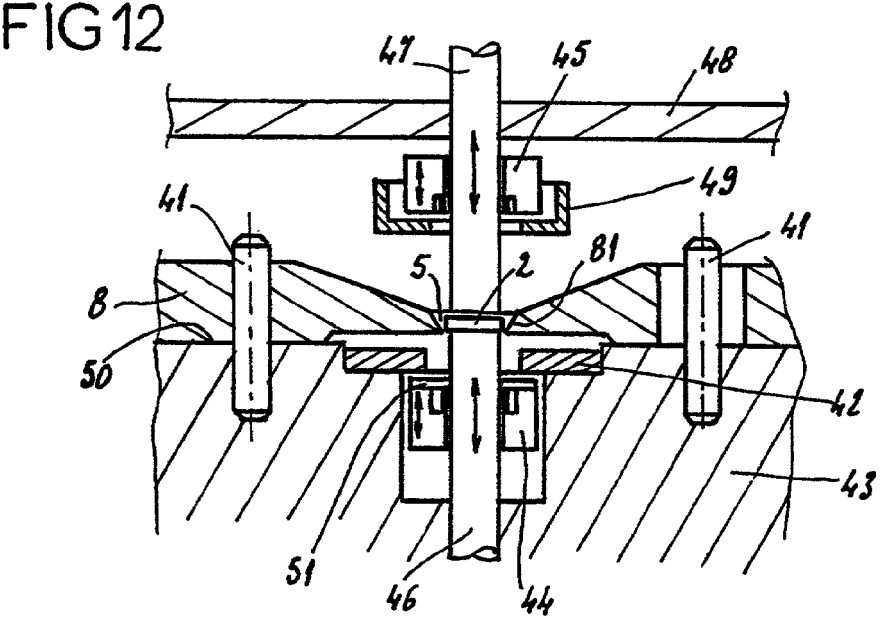
FIG. 12 diagrammatically represents a test rig for the adhesive bonding.

A test rig was prepared, making it possible to deposit an adhesive seal between the biochip 2 and the container 8. This test rig is represented diagrammatically on FIG. 12.

A lower base 43 is equipped with a ring light 44, the height of which can be adjusted manually, placed around the support 46 for the biochip 2. The ring light 44 is protected by an interchangeable quartz lens, when the adhesive would run onto the ring during the tests. The biochip 2 is maintained, by vacuum, on its support 46, the height of which can also be adjusted manually. This base is designed to also receive a consumable or single-use element which plays the role of the container 8, and which is positioned with two reference pins 41. An interchangeable heat mask 42 makes it possible to illuminate the adhesive seal 5 and to protect the biochip 2 depending on its aperture. An upper block 48 takes the form of a removable lid. It is equipped with a ring light 49 which allows the adhesive seal 5 to be illuminated from above the container 8. The ring light 49 is identical to that 44 of the base 43. An upper finger 47 makes it possible to protect the active surface of the biochip, without contact between this finger and the biochip 2. The height of this finger can be adjusted manually. The element 8 can be adjusted in the x, y directions over the surface 50, using the reference pins 41. The UV light originates from two light sources of the SUFERLITE SUV-DC-P type from the company Lumatec, each having a power of 200 W. An adhesive distributor, like that described with reference to FIG. 10, of the internal pressure type, is mounted along the z axis of an AUTOPLACE 420 robot from the company Sysmelec (Neuchatel, Switzerland), via an attachment which makes it possible to incline the needle. The robot is controlled by an AUTOPLACE control organ from the company Sysmelec, and the parameters of the assembly and adhesive bonding process are controlled by a microcomputer. The needle for distributing the adhesive is a Teflon® needle. The adhesive is metered according to the pressure/time principle, i.e. a given pressure is applied for a given time.

The consumable element 8 is produced by machining using a plastic material made of polystyrene, with a window 81 which is variable in size. The window of the container has a square cross section which is 5.717 mm±0.05 or 5.577 mm±0.05, or 5.437 mm±0.05 in size.

The biochip 2 has, as a support, a glass square which is 5.37 mm±0.18 in size and 0.7 mm thick.

Four adhesives, in particular based on acrylates, for example urethane acrylates, were tested: the Dymax 128M, Dymax 1-20280, Loctite 3104 and Loctite 3105 adhesives. The tests carried out show that a value of 0.8 bar ($8 \times 10^4$ Pa) as the pressure for metering the adhesive makes it possible to correctly control this metering. The needle is used in the vertical position, since this position makes it possible to have a minimum distance between the tip of the needle and the biochip/container interface. The amount of adhesive used for the various tests is a few $mm^3$ per adhesive seal.

In a first series of tests, the adhesive is pre-cured from below for 10 seconds, and then cured from above for 20 seconds.

In a second series of tests, the adhesive is pre-cured from below for 5 seconds, and then cured from above for 20 seconds.

In a third series of tests, the adhesive is pre-cured from below for 10 seconds, and cured from above for 2 minutes.

All the tests show, by analysis under a microscope, that the adhesive seal 5 has a very good visual appearance, i.e. its contour around the biochip is characterized by a very homogeneous geometry and there is no adhesive either on the active surface of the biochip or on the opposite face.

Even with the shortest curing time, which corresponds to the second series of tests, it is possible to transfer the entire container/biochip combination without risk of moving the biochip.

EXAMPLE 2

Figure 13:
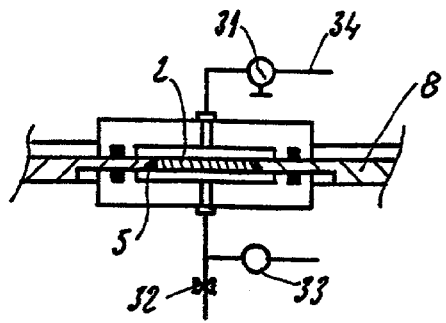
FIG. 13 diagrammatically represents the test rig for the mechanical resistance tests and tests for leaktightness.

Test for Mechanical Resistance and for Leaktightness of the Attachment of the Biochip to the Container by Adhesive Bonding A test rig was designed to validate the consumable elements bonded, by measuring the mechanical resistance and the leaktightness. In this test rig, the consumable elements are trapped between two plates which form a cavity on either side of the biochip 2. The measurement is taken according to the differential pressure principle, which ensures good reliability of measurement. The measuring cavity is temperature controlled. The test rig is represented diagrammatically on FIG. 13.

After having introduced a buffer (25 mM sodium carbonate, pH 10, sold by the company Radiometer Analytical Villeurbanne, France, under the reference S11M007) onto one of the faces of the biochip, the test consists in exposing the device to a pressure of 900 mbar and to a temperature of 80° C. for cycles of 30 minutes. The lack of variation on the two manometers 31 and 33 is a first indication of the resistance and of the leaktightness of the attachment means 5. The gaseous circuit comprises an inlet valve 32 and an outlet valve 34. A second visual control may be carried out by opening the test rig in order to verify that there is no liquid on the other face of the biochip.

The biochip 2 has a support 9 in the form of a glass square 5.37 mm±0.18 in size and 0.7 mm thick.

The window of the container has a square cross section 5.717 mm±0.05 or 5.577 mm±0.05 in size. This container is made of black polystyrene.

The adhesive used is the Dymax adhesive 1-20-280 or Loctite 3104 adhesive.

The conditions chosen are representative of extreme conditions for reactions between ligands and analytes since, for example, in the immunoassays field, the reaction temperature is often close to 37° C. In the nucleic acids domain, the temperature may vary between room temperature and 95° C., but the 95° C. temperatures are denaturing temperatures which are required for short periods of time, of the order of a few minutes. Hybridization reactions generally take place between 30 and 60° C. Table I below summarizes the results obtained.

TABLE I

| Adhesive (5) | Window (81) | Number of tests (reproducibility) | Visual control after 30 minutes | Time during which the pressure does not vary |
|---|---|---|---|---|
| Dymax 1-20-280 | 5.717 mm | 4 | Positive | >230 minutes |
| Dymax 1-20-280 | 5.577 mm | 2 | Positive | >230 minutes |
| Loctite 3104 | 5.717 mm | 2 | Positive | >230 minutes |
| Loctite 3104 | 5.577 mm | 4 | Positive | >230 minutes |

Independent tests are carried out in each scenario in order to verify the reproducibility of the results.

The tests carried out with a buffer at pH 6.0 (100 mM potassium phosphate, pH 6.0) produce results similar in terms of resistance.

The tests carried out with temperatures of 60° C. increase the resistance times.

In all cases, the mechanical resistance and the leaktightness resistance are greater than 230 minutes, which indicates that the attachment means according to the invention is completely compatible with the reaction times commonly used in reactions between ligands and analytes.

The set of tests carried out demonstrates that the attachments means according to the invention can be automated, from the point of view of both the quality of the product and the conditions for producing a reliable automatic machine.

What is claimed is:

1. A device for analyzing at least one analyte, comprising:
   a container;
   a biochip comprising:
      an active face including an active surface onto which are distributed and bound a plurality of ligands used for the analysis and a peripheral zone,
      at least one face opposite to the active face, and
      a transverse peripheral strip connecting the active and opposite faces and comprising several sides; and
   an attachment means placed on opposite lateral sides of the active face of the biochip and connecting the transverse peripheral strip of the biochip, excluding any other part, face or surface of the biochip, to the container, completely exposing the peripheral zone of the active face of the biochip, the attachment means including means that are flexible at a level of the transverse peripheral strip and exert a pressure on the transverse peripheral strip of the biochip to facilitate positioning and/or maintaining in position of the biochip, the container and the biochip delimiting a reaction compartment, the biochip being in contact with the container only via the attachment means.

2. A device for analyzing at least one analyte, comprising:
a container having a window:
a biochip comprising:
   an active face including an active surface onto which are distributed and bound a plurality of ligands used for the analysis and a peripheral zone,
   at least one face opposite to the active face, and
   a transverse peripheral strip connecting the active and opposite faces, comprising several sides; and
an attachment means placed on opposite lateral sides of the active face of the biochip that attaches the biochip to the container through the window, the attachment means including means that are flexible at a level of the window and exert a pressure on the transverse peripheral strip of the biochip to facilitate positioning and/or maintaining in position of the biochip, the biochip and the container delimiting a reaction compartment, the attachment means of the biochip connecting the transverse peripheral strip of the biochip excluding any other part of the biochip, to a frame of the window of the container in order to expose the peripheral zone of the active face of the biochip.

3. The device as claimed in claim 2, characterized in that the frame of the window has an edge parallel to the transverse strip of the biochip.

4. The device as claimed in claim 1, characterized in that the attachment means completely exposes the active face.

5. The device as claimed in claim 4, characterized in that the active surface merges with the surface of the active face.

6. The device as claimed in claim 1, characterized in that the attachment means is an adhesive.

7. The device as claimed in claim 2, characterized in that the container window has a transverse profile substantially identical to that of the biochip.

8. The device as claimed in claim 2, characterized in that the window of the container is equipped with a means for allowing a surplus of adhesive to be stored without the adhesive overflowing onto the peripheral zone of the biochip.

9. The device as claimed in claim 8, characterized in that the means for allowing a surplus of adhesive consists of a beveled shape at a level of the window of the container.

10. The device as claimed in claim 7, characterized in that an interstice between the border of the window and the transverse strip of the biochip is between 2 mm and 0.05 mm, advantageously between 0.5 mm and 0.05 mm, and preferentially between 0.2 mm and 0.1 mm.

11. The device as claimed in claim 1, characterized in that the attachment means extends along the entire transverse strip of the biochip.

12. The device as claimed in claim 1, characterized in that the attachment means connects two opposite zones of the transverse strip, to the container.

13. The device as claimed in claim 6, characterized in that the adhesive comprises a component which can be cured by ultraviolet radiation.

14. The device as claimed in claim 1, characterized in that the biochip is a parallelepiped, the active and opposite faces of which are each rectangular or square.

15. The device as claimed in claim 1, characterized in that the reaction compartment is arranged so as to bring a liquid medium, subjected to the analysis, and the active surface of the biochip into contact.

16. The device as claimed in claim 15, characterized in that the attachment means ensures that the reaction compartment is leaktight with respect to the outside.

17. The device as claimed in claim 1, characterized in that the active surface of the biochip has a surface area of less than 100 $mm^2$ advantageously less than 65 $mm^2$, and preferentially less than 30 $mm^2$.

18. The device as claimed in claim 1, characterized in that the active surface of the biochip represents at least 75% of the surface area of the active face.

19. The device as claimed in claim 1, characterized in that the ligands are nucleic acids.

20. The device as claimed in claim 8, characterized in that the means for storing a surplus of adhesive consists of a concavity present on all or part of the surround of the window of the container.

21. The device as claimed in claim 1, characterized in that the flexible means consist of two interdependent components, namely an intermediate component inclined relative to the opposite face of the biochip, and an end component substantially perpendicular to the opposite face, the end component exerting a pressure on the transverse strip of the biochip.

22. The device as claimed in claim 1, characterized in that the flexible means comprise claws, the cross section of the claws being substantially triangular.

23. A process for attaching a biochip to a container, for producing an analytical device as claimed in claim 1, characterized in that the biochip is maintained opposite the container, in that a liquid adhesive seal is distributed between the transverse strip of the biochip and the container, and in that the adhesive is cured by ultraviolet radiation.

24. The attachment process as claimed in claim 23, wherein the container includes a window having a frame, characterized in that the biochip is positioned relative to the container so as to place the transverse strip of the biochip opposite the frame of the window of the container.

25. The attachment process as claimed in claim 24, characterized in that the at least one of the biochip and the container is maintained on a positioning means by applying a vacuum.

26. The attachment process as claimed in claim 23, characterized in that ultraviolet radiation is applied to the adhesive seal on at least one of the faces of the analytical device.

27. The attachment process as claimed in claim 23, characterized in that a mask is positioned between the biochip and the ultraviolet radiation in order to protect the ligands.

28. The device as claimed in claim 2, characterized in that the flexible means consists of two interdependent components inclined relative to the opposite face of the biochip, and an end component substantially perpendicular to the opposite face, the end component exerting a pressure on the transverse peripheral strip of the biochip.

* * * * *